US010080999B2

(12) United States Patent
Douglas et al.

(10) Patent No.: US 10,080,999 B2
(45) Date of Patent: Sep. 25, 2018

(54) SAMPLE VESSEL AGITATION APPARATUS AND METHOD

(71) Applicant: TTP LABTECH LTD, Royston (GB)

(72) Inventors: Anthony Douglas, Cambridgeshire (GB); Gary Cochrane, Bedfordshire (GB); Robert Bumstead, Cambridgeshire (GB)

(73) Assignee: TTP LABTECH LTD., Royston (GB)

( * ) Notice: Subject to any disclaimer, the term of this patent is extended or adjusted under 35 U.S.C. 154(b) by 149 days.

(21) Appl. No.: 15/110,901

(22) PCT Filed: Jan. 16, 2015

(86) PCT No.: PCT/GB2015/050096
§ 371 (c)(1),
(2) Date: Jul. 11, 2016

(87) PCT Pub. No.: WO2015/107359
PCT Pub. Date: Jul. 23, 2015

(65) Prior Publication Data
US 2017/0014787 A1    Jan. 19, 2017

(30) Foreign Application Priority Data

Jan. 17, 2014   (GB) .................................. 1400836.1
Nov. 28, 2014   (GB) .................................. 1421201.3

(51) Int. Cl.
*B01F 7/00*       (2006.01)
*B01F 11/00*      (2006.01)
(Continued)

(52) U.S. Cl.
CPC ...... *B01F 11/0005* (2013.01); *B01F 7/00258* (2013.01); *B01F 7/1605* (2013.01);
(Continued)

(58) Field of Classification Search
USPC ........................................................ 366/198
See application file for complete search history.

(56) References Cited

U.S. PATENT DOCUMENTS 3,347,531 A   10/1967   Strong et al.
3,776,700 A   12/1973   Gallant
(Continued)

FOREIGN PATENT DOCUMENTS

EP    1318408    6/2003
GB    1545538    5/1979
(Continued)

OTHER PUBLICATIONS

International Preliminary Report on Patentability, Application No. PCT/GB2015/050096, dated Jul. 19, 2016.
(Continued)

*Primary Examiner* — Mark Halpern
(74) *Attorney, Agent, or Firm* — Barnes & Thornburg LLP

(57) ABSTRACT

An agitation device for agitating products held in wells of sample vessels or a laboratory microplate is disclosed. The device is arranged to retain a microplate and to agitate an agitation member comprising an array of agitation projections which enter the wells of the microplate. The agitating motion can be horizontal and damping means can be provided between an actuator and parts of the device to reduce overall vibrations. A related method of agitation of microplate or sample vessel contents is described. A novel arrangement for receiving a replaceable agitation member for the device is also disclosed.

20 Claims, 13 Drawing Sheets

(51) Int. Cl.
  *B01F 7/16*   (2006.01)
  *B01F 7/18*   (2006.01)
  *B01F 13/10*   (2006.01)
  *B01F 15/00*   (2006.01)
  *B01L 3/00*   (2006.01)
  *G01N 35/00*   (2006.01)

(52) U.S. Cl.
  CPC ............ *B01F 7/18* (2013.01); *B01F 11/008* (2013.01); *B01F 11/0088* (2013.01); *B01F 11/0091* (2013.01); *B01F 13/1022* (2013.01); *B01F 15/00201* (2013.01); *B01F 15/00383* (2013.01); *B01F 15/00389* (2013.01); *B01F 15/00662* (2013.01); *B01L 3/5085* (2013.01); *B01F 2215/0037* (2013.01); *B01L 2300/0829* (2013.01); *G01N 2035/00534* (2013.01)

(56) References Cited

U.S. PATENT DOCUMENTS

| | | | |
|---|---|---|---|
| 6,112,603 | A | 9/2000 | Pietilae et al. |
| 2004/0031333 | A1 | 2/2004 | Buckner, III |
| 2005/0034849 | A1 | 2/2005 | Oldenburg |
| 2005/0277184 | A1 | 12/2005 | Bargh |
| 2007/0177457 | A1 | 8/2007 | Hafner |

FOREIGN PATENT DOCUMENTS

| | | |
|---|---|---|
| JP | H0189364 | 6/1989 |
| JP | 2010127696 | 6/2010 |
| WO | 0216838 | 2/2002 |
| WO | 2014058880 | 4/2014 |

OTHER PUBLICATIONS

United Kingdom Search Report, Application No. GB1421201.3, dated Jan. 14, 2015.
United Kingdom Examination Report, Application No. GB1400836.01, dated Jun. 23, 2014.
International Search Report, Application No. PCT/GB2015/050096, dated Jun. 26, 2015.
International Written Opinion, Application No. PCT/GB2015/050096, dated Jun. 26, 2015.
John Comley, Microplate Mixing, Winter 2007, available from http://www.ddw-online.com/enabling-technologies/p92837-microplate-mixing-winter-2007.html, last retrieved on Apr. 12, 2018, 8 pages.
Mixing Products Summary, dates of availability unknown, at least available by Jul. 11, 2016, 1 page.
Method for Generating Mixing Effects in Microplates, date published unknown, at least available by Jul. 11, 2016, 1 page.

SAMPLE VESSEL AGITATION APPARATUS AND METHOD

CROSS REFERENCE TO RELATED APPLICATIONS

This application is a U.S. nationalization under 35 U.S.C. § 371 of International Application No. PCT/GB2015/050096, filed Jan. 16, 2015, which claims priority to United Kingdom Application No. 1400836.1 filed Jan. 17, 2014, and United Kingdom Application No. 1421201.3 filed Nov. 28, 2014.

FIELD OF THE INVENTION

The present invention relates to the mixing of products held in laboratory microplates or sample vessels. In particular, the invention relates to the mixing of liquids held in wells of laboratory microplates using a relative stirring motion.

BACKGROUND OF THE INVENTION

Microplates are commonly used for holding products, often liquids, for laboratory testing. A microplate is generally formed as a substantially flat plate, with multiple "wells" formed in the plate, which are used as relatively small-volume test-tubes in laboratory experiments and processes. Such microplates are used in analytical research and clinical diagnostic testing laboratories and can commonly be used in the enzyme-linked immunosorbent assay, which is a widely used method of modern medical diagnosing testing. Sample tubes are often used in similar circumstances and can be held in an array in a rack or holder arrangement to provide an array of sample vessels arranged similarly to wells of a microplate.

Wells in a microplates typically hold between a few tens of nano-liters, up to several milliliters of a liquid. Microplate wells can be of many shapes, having typically circular, oval, square, or rectanguloid openings as viewed from a direction perpendicular to the plate.

The types of products, fluids, emulsions or liquids stored and tested in the wells can vary in viscosity, composition, volume and in the number of separate components or ingredients making up the liquid. In some applications, the liquid added to the wells is pre-mixed and is simply provided to the wells in a ready-mixed state. Mixing during the time in which the liquid is in the wells may still be desirable to prevent separation of components in the liquid, for example. In other applications, a number of different liquids, products or ingredients may be added to wells of the plate in separate steps and in this case, it is often desirable to mix the products after they have been added to the micro plate. In other applications, it is desirable to mix the liquids either after they have been added to the micro plate in order to ensure that the contents do not separate over time, or to ensure that any reaction or treatment of the ingredients in the plate happens in a uniform manner throughout the volume of each well.

A number of solutions to the problem of in-well mixing have been proposed. These include some of the following technologies. Magnetic fields can be used to rotate rotatable metallic members, which are suspended in a rotatable configuration in each well. Metallic balls may be levitated and allowed to fall in the liquid to agitate it, by the use of magnetic fields. In this case, only the magnetic ball is in contact with the fluid. Pin members may be used to transfer ultrasonic vibrations into the liquids to mix them. Pulsating gas streams may also be use to agitate the liquids in the wells. Other contact-free, methods exist, in which the plate itself may be agitated by orbital movement of the plate to induce agitation due to inertia in the liquids in the wells. In other applications, surface acoustic waves (SAW) can be used to induce circulating currents in the well plates. Adaptive focused acoustics (AFA) are an alternative to surface acoustic waves. AFA act to focus acoustic vibrations onto a sample vessel from outside the sample vessel by use, for example, of a concave acoustic transducer, where the focus point of the acoustic waves generated is located at a focal point, the sample vessel being located at the focal point of the waves. The above arrangements have certain drawbacks and are not suited to all circumstances in which well-plate mixing is necessary. Similar issues apply in the mixing of samples in other vessels, such as sample tubes, which are often carried in arrays in a similar form or layout to wells of laboratory well plates. The present invention therefore seeks to overcome certain drawbacks of the prior art.

SUMMARY OF THE INVENTION

Techniques using magnetic fields can be relatively expensive to implement and require the use of potentially complex and expensive equipment to generate the magnetic fields. Metallic components are necessary such that the stirring members are moved under the influence of the generated magnetic fields. This can result in an expensive overall assembly and metals may, in some applications, be undesirable. Pulsating gas streams also require relatively cumbersome generating equipment for generating a gas under pressure. Ultrasonic vibrations require relatively expensive equipment for generating the ultrasonic vibrations. Similarly, the equipment required to generate surface acoustic waves or adaptive focused acoustics can be complex and expensive to manufacture, and can be sensitive to the specific design dimensions or materials of the target sample vessel. Where mixing is induced by orbital movement of the well plate, the degree of mixing achievable is limited by an upper limit of movement before liquid starts to spill out of the individual wells due to over-agitation.

A first aspect of the invention provides an agitation device, for agitating products held in an array of sample vessels, comprising:
  a body, comprising a vessel receiving area, adapted to receive an array of sample vessels holding the products to be agitated;
  actuating means, for creating an agitating motion; and
  an agitation member receiving member, connected to the actuating means, and arranged to receive an agitation member comprising an array of agitation projections, the projections being arranged to enter the sample vessels;
  wherein the device is arranged to hold the vessels substantially still relative to the body and to induce an agitating motion in the array of agitation members via the agitation member receiving member, to agitate products in the sample vessels.

The invention is advantageous compared to other known devices, in which the sample vessels, or a well plate comprising the sample vessels, is agitated, which can result in spillage of the products from the vessels when a high level of agitation is applied. This is because the whole mass of the products to be agitated in the vessels is moved in prior methods, and so there is a greater likelihood of the products being ejected from the vessels. Greater agitations can be applied by agitation of the agitating projections of the invention, while retaining the vessels substantially still, which can allow increased mixing while reducing the risk of products being inadvertently ejected from the wells. It will be apparent to the skilled reader from a full reading of the present disclosure that the sample vessels of the invention can, for example, be wells in a well plate or may be separate sample vessels, such as sample tubes or microtubes, held in an array, preferably in a support or rack configured for this purpose. The invention is therefore described in parts of the following with reference to wells in microplates, but it will be apparent to the skilled reader that a well in a well plate or microplate can be replaced by a sample tube held in a suitable support. An array of wells in a microplate can equally be replaced by an array of sample vessels or tubes in a suitable support. The actuating means of the invention can be activated at varying speeds to induce varying rates of agitation. The device can be arranged to receive replaceable agitation members, to allow cleaning or disposal of the agitation member and its projections which contact the material to be agitated.

The device of the present invention provides an efficiently constructed relatively low-cost device, which provides maximum mixing whilst reducing risks of spillage of the liquid in the wells. The invention allows greater adaptability to different well sizes, dimensions and shapes. The invention therefore seeks to provide an alternative device to address the drawbacks of the known techniques for microplate mixing.

The agitation device may therefore further comprise an agitation member comprising an array of agitation projections, the projections being arranged to enter the wells of the microplate or the array of sample vessels, the agitation member being mounted to the agitation member receiving member. The device can be a microplate content agitating device where it is arranged in a manner suitable to agitate the contents of a microplate.

The actuating means of the agitation device may comprise an actuator, preferably a rotary actuator, which is connected between the body of the device and the agitation member receiving member, to create a directly driven agitating motion in the agitation member receiving member relative to the body. This direct driving connection gives more direct control over the motion of the agitation member receiving member and any agitation member attached thereto. This can be advantageous over devices which use vibratory means, such as oscillating or rotating eccentric masses, since the motion is less dependent upon resonance and related natural frequencies of the device or parts thereof.

The agitation member receiving member may be mounted to the body by a translational coupling. Such a translational coupling can be arranged to permit translational motion of the agitation member receiving member relative to the body, but to substantially inhibit rotational motion of the agitation member receiving member relative to the body. This allows a direct rotational drive input to create a translating motion in the agitation member receiving member, in a substantially circular path, whilst avoiding rotation of the agitation member receiving member relative to the body. In this way agitation members such as pins, connected to the device can be made to describe a circular path to form a stirring motion in the sample vessels by a single rotational input from a device such as a motor.

The translational coupling may comprise a plurality of flexible connections between a movable portion of the device and a fixed portion of the device. The translational coupling may comprise a plurality of resilient members connecting the body to the agitating member receiving member.

The translational coupling may comprise a plurality of leaf springs arranged between a movable portion of the translational coupling and a fixed part of the translational coupling. The fixed part may be a fixed outer frame.

The leaf springs may be arranged to be relatively flexible in a plane of the agitating motion of the device and to be substantially stiff in a direction perpendicular to the plane of the agitating motion of the device to support the agitation member at a fixed distance from the plane of the array of vessels. For example, the leaf springs may have a greater dimension in a direction perpendicular to the plane of the array of vessels, to create increased stiffness in that direction, while having a thinner dimension in a direction perpendicular to the plane of the vessels, so that they are freer to flex in that direction parallel to that plane of the array of vessels.

The actuating means may be fixedly mounted to the body and may be rotatably connected to the agitation member receiving member. This allows a rotating shaft of the actuating means, which may be eccentrically formed or may have a cam profile for inducing a cyclical agitating motion, to induce the desired stirring motion.

In a second aspect, the invention provides an agitation device, for agitating products held in wells of a multi-well microplate or in an array of sample vessels, comprising:
 a body, comprising a microplate or vessel receiving area, adapted to receive a microplate or an array of sample vessels for holding the products to be stirred;
  actuating means, for creating an agitating motion; and
  an array of agitation members arranged to enter the wells of the microplate or the vessels and connected to the actuating means;
 wherein the actuating means comprises a rotary actuator for creating a rotary motion in the array of agitation members.

The rotary actuator can induce a rotary agitation motion in the agitation member, while reducing vibrations transmitted to the body of the device.

The actuating means of the invention can therefore comprise a rotary oscillator for creating a rotary stirring motion in the agitation member.

The agitation motion induced in the agitation member may preferably induce a translational motion so that the member describes a cyclical or rotational path, but does not itself rotate. The device may be configured to inhibit rotation of the agitation member itself, while permitting a cyclical translational motion of the agitation member and/or its agitation projections.

The agitation device may further comprise a sensor for detecting a resonant frequency in the agitation device and a controller arranged to control actuating means of the agitation device to maintain the agitating motion at the resonant frequency, in response to input from the sensor.

The agitation or stirring motion may be induced in a plane substantially parallel to a principal plane of the microplate or to the array of sample vessels. This can allow products in the microplate or in the array of sample vessels to be displaced in a circular motion to stir them in the wells. The stirring motion may be induced in a substantially horizontal plane of the device.

The device may further comprise vibration damping means located between the actuating means and the body. This can reduce unwanted vibrations transmitted outside the oscillating portions of the device.

The device may further comprise an agitation member receiving member arranged to both receive and retain the agitation member. This can help to facilitate removal, replacement and retention of the agitation member on the device.

The vibration damping means may be arranged to connect the agitation member receiving member to the body. This provides a dual function of the damping means, reducing components and simplifying manufacture, thus reducing cost.

The actuating means may be mounted to the agitation member receiving member. This can permit more direct transmission of vibrations from the actuator to the agitation member. The vibration damping means may comprise resilient material.

The device may further comprise secondary vibration damping means for damping vibrations transmitted from the body of the device to a surface upon which the device is mounted. This can further reduce noise and vibration transmitted to the surrounding environment. The secondary vibration damping means may comprise feet arranged to be mounted between the body of the device and a surface on which the device is intended to be placed for use to help facilitate this.

The device may have first and second configurations;
the first configuration permitting the microplate or vessels and/or the array of agitation members to be removed from the body; and
the second configuration maintaining the agitation members in the wells of the microplate or in the vessels to stir the liquid in the wells or vessels.

The dual configurations can allow the device to operate in the second configuration and move to the first configuration to allow removal and/or replacement of the vessels or microplate and/or the agitation member.

The device may be arranged to change between the first and second configurations by relative movement of the microplate or vessel receiving area and an agitation member receiving member, toward and away from one another.

The relative movement of the microplate or vessel receiving area and the agitation member receiving member may be provided by a linear track and a corresponding track engaging member.

The linear track may be provided on the body of the device and the track engaging member may be provided on a microplate or vessel receiving member comprising the microplate or vessel receiving area.

The linear track may comprises linear actuation means for moving at least one of the microplate or vessel receiving area and the agitation member receiving member along the track.

The agitation member may comprise a plate comprising the array of agitation projections. The agitation member may comprise an array of pins. This can provide an efficient construction to allow insertion of the pins in to the wells of the microplate or into the sample vessels.

The device may further comprise releasable retaining means, for releasably retaining the agitation member on the device. This can further facilitate removal and/or replacement of the agitation member.

In a third aspect, the invention provides an agitation member receiving member, for an agitation device of the first aspect, comprising:
at least one fixed engaging member for engaging a first side of the agitation member; and
at least one biasing member for engaging a second side of the agitation member and arranged to bias the agitation member toward the fixed engaging member to retain the agitation member on the agitation member receiving member.

The claimed configuration allows the easy removal, refitting or replacement of the agitation member between agitation operations.

The biasing member may be configured to provide a biasing force having first and second components:
the first component biasing the agitation member toward the engaging member in a first direction; and
the second component biasing the agitation member in a second direction different from the first, to retain the agitation member on the receiving member.

This allows the biasing member to both retain a first side of the agitation member against the engaging member and also retain a second side of the agitation member against the receiving member in a second direction. Such an arrangement can permit easy release and retention of the agitation member in a cost effective assembly.

The first direction may be substantially parallel to a principal plane of the agitation member. This helps to retain it laterally against an engagement member. The second direction may be substantially perpendicular to the principal plane of the agitation member. This can help to retain the agitation member against the receiving member in a second direction.

The biasing member or members may have first and second engagement regions for engaging the agitation member, the first and second regions arranged such that:
when the agitation member engages the first engagement region of the biasing member, the biasing member biases the agitation member toward the receiving member; and
when the agitation member contacts the second region of the biasing member, the biasing member biases the agitation member away from the receiving member.

Such an arrangement can facilitate both retention of the agitation member in the device and quick release and replacement or re-installation of the agitation member.

The biasing member may comprise first and second engagement regions which are differently angled portions of a biasing element, separated by a curve, a ridge or a peak in the biasing element.

The agitation member receiving member may further comprise plural engaging members for retaining the agitation member. The agitation member may further comprise plural biasing members arranged to bias the agitation member toward the engaging member or members, to retain the agitation member. Multiple engaging members and/or biasing members can help to improve the stability and retention of the agitation member in the device during agitation.

A gap may be provided between adjacent biasing members, for allowing a user to grasp the agitation member to extract the agitation member from the receiving member. This facilitates removal while providing the improved retention and stability of plural biasing members.

The receiving member may comprise a primary biasing member arranged to provide a first biasing force biasing the agitation member toward the fixed engaging member, and a secondary biasing member may be arranged to provide a second biasing force, biasing the agitation member in a second direction, different from the first direction. The first and second biasing forces may each be arranged in a plane of the agitation member. Such an arrangement can be particularly beneficial with laboratory microplates or sample supports which are manufactured with dimensions specified from one registration corner, which may be located at, near to, or at a fixed point relative to, an intersection of two straight sides of the microplate or sample support. A fixed registration point can therefore be provided at one corner of the microplate or vessel receiving area, which is at a fixed location relative to the registration point of the microplate or vessel array. Additionally or alternatively, a similar arrangement can be provided for the agitation member, to align it to a registration point and to enable its accurate alignment with the wells of the microplate or with the vessels. This can permit the microplate or vessels and/or agitation member to be accurately aligned with the relevant registration corner and thus distances from points on the microplate or vessels and/or agitation member can be determined relative to this registration corner. The primary biasing member can therefore bias the agitation member toward a first registration surface of the receiving area and the secondary biasing member can bias the agitation member toward a second registration surface, arranged in a different direction from the first registration surface. This provides 2 dimensional alignment of the agitation member in the agitation member receiving area. Further, e.g. third or more, biasing members and registration surfaces may be provided to align the microplate or vessels in a third dimension. A similar arrangement can be provided in the microplate or vessel receiving area to bias the microplate and registration surfaces to provide a corresponding microplate or vessel array registration function.

The agitation member may further comprise a central projecting portion for engaging a central portion of the agitation member, the central projecting portion comprising at least one sloped surface for allowing the agitation member to slide over the central projecting portion when introduced onto the receiving member.

The agitation device may comprising an agitation member receiving member as described herein, although the receiving member can be employed in any similarly arranged agitation device.

In a further aspect, the invention provides a method of agitating products in wells of a multi-well microplate or an array of sample vessels, comprising the steps of:
  providing a microplate having a plurality of wells or an array of sample vessels, each well or vessel containing at least one product to be agitated;
  providing an array of agitating projections on an agitation member and entering the vessels or the wells of the microplate; and
  inducing an agitating motion in the array of agitating projections, via the agitation member, while maintaining the microplate or vessels substantially still.

The agitating motion may be a horizontal agitating motion. This can help to reduce vibrations transmitted from vibrating parts to the body of the device and on to the surrounding environment and can therefore reduce noise.

The agitating motion may be a rotary motion created with a rotary oscillator. This can be a low cost and efficient way of creating the agitating motion. Methods of the invention can be carried out using the device described herein and incorporating any of the means and steps described herein. The invention further provides a device arranged to carry out the methods of the invention.

The agitating motion may be induced by a direct drive connection between a main body of an agitating device and the agitation projections. This provides greater control over the exact agitating motion which is induced.

The method may comprise detecting a resonant frequency of an agitation device creating the agitating motion and controlling actuating means of the agitation device to maintain the agitating motion at the resonant frequency. This can enable the agitating motion to be created in the most efficient manner with the greatest agitating motion created for a given drive input.

An agitation member for the invention may comprise a connecting portion for connecting the agitation member to an agitation device; a plurality of agitating projections for entering wells of the microplate or the vessels. The projections may have a variety of forms. The paddles may have a substantially planar end, or a paddle-like form, where an elongate support portion is tipped with a substantially planar end portion. The end portion may have a width greater than that of the elongate support portion.

The invention further provides an agitation device, for agitating products held in wells of a multi-well microplate, comprising:
  a body, comprising a microplate receiving area, adapted to receive a microplate for holding the liquid to be agitated;
  actuating means, for creating an agitating motion; and
  an agitation member receiving member, connected to the actuating means, and arranged to receive an agitation member comprising an array of agitation projections, the projections being arranged to enter the wells of the microplate;
wherein the device is arranged to hold the microplate substantially still relative to the body and to induce an agitating motion in the array of stirring members via the agitation member receiving member, to agitate products in the wells of the microplate.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
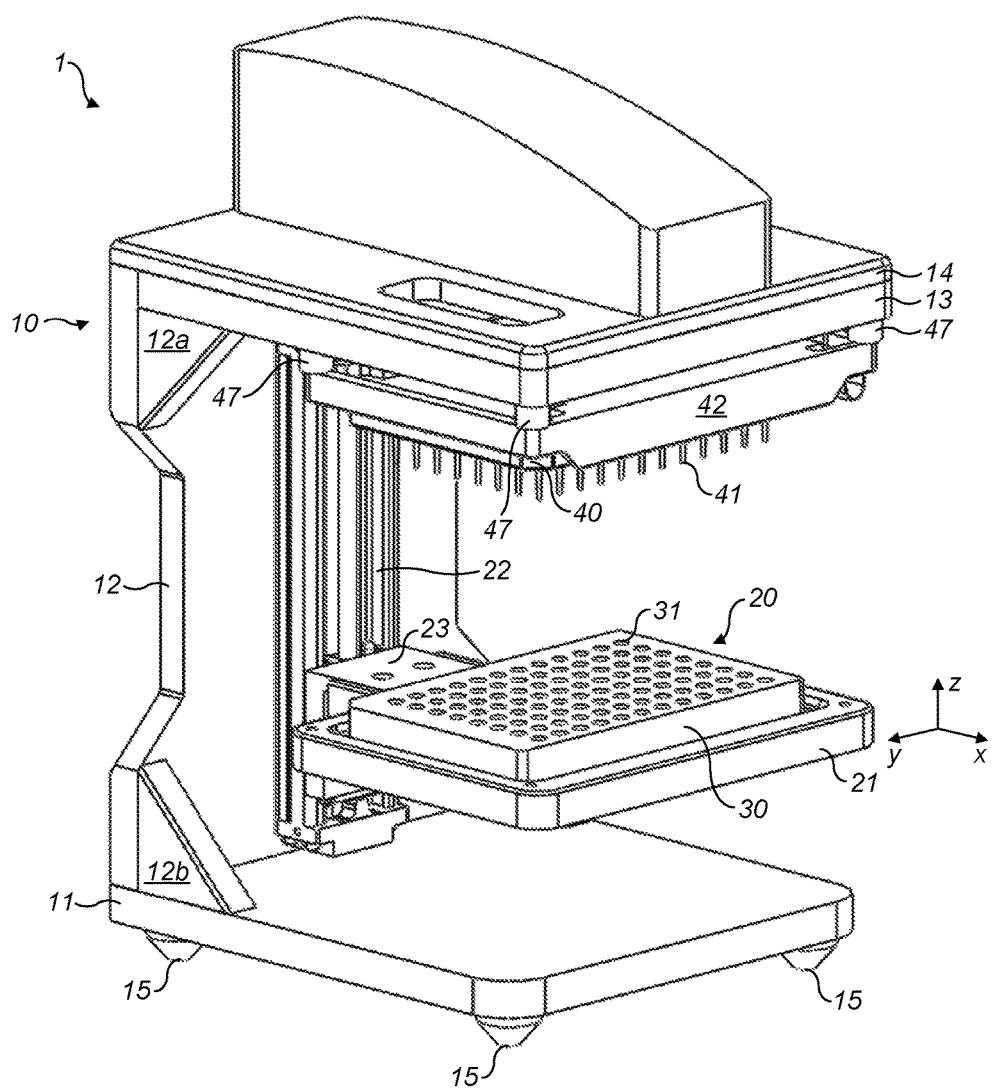
FIG. 1 shows an isometric view of device according to the present invention.

FIG. 1 shows a device according to the present invention. It will be apparent to the skilled reader that where the following specific description of embodiments refers to a microplate, that the microplate could be replaced or combined with an array of sample vessels held in sample vessel retaining means, to stir or agitate samples in the sample vessels as well as or instead of samples held in wells of a microplate. Wells of a microplate can also be sample vessels, for the purposes of the disclosure. The device has a body 10, which comprises a microplate receiving area 20. The body 10 comprises a base plate 11, an upright element 12 and an upper horizontal member 13. A cover 14 is provided on the upper horizontal member, within which actuation components of the device are enclosed, which will be described in more detail later. Corner braces 12A and 12B are provided to increase rigidity of the connection between the upright member 12 and the base plate 11 and between the upper horizontal member 13 and upright member 12. The upper horizontal member 13 is therefore connected to base plate 11 via an upright portion 12, which may be either integrally formed with either or both of the upper horizontal member 13 and base plate 11, or may be manufactured from separate parts and connected via suitable fixing means, such as glue, bolts, welding, screws or any other suitable attachment means. Base plate 11 comprises feet 15. Feet 15 can be manufactured from vibration absorbing or damping materials, such as rubber, silicon or other resilient materials, in order to isolate or damp vibrations induced in base plate 11 from a surface on which the device 1 is placed.

Microplate receiving area 20 comprises a substantially rectanguloid area arranged to receive a laboratory microplate, and to retain it in a relatively fixed position in receiving area 20. The receiving area can be located on a height-adjustable receiving member, which in the specific illustrated embodiment is provided as a height adjustable platform 21. The receiving member can comprise a substantially planar body, having a recess which is arranged to receive a microplate and to prevent lateral translation of the microplate 30 with respect to the receiving member 21.

The device 1 will generally be used in the orientation shown in FIG. 1, to retain products in wells 31 of the microplate 30 by gravity. The axis marked Z in FIG. 1 therefore represents an upward direction, with gravity acting in the opposite direction to retain the products to be mixed in the openings 31 in the wells of the microplate 30. References to upward and downward directions or motion therefore refer to movement along the axis marked Z in FIG. 1, while references to lateral movement refer to movement in the directions marked X and Y in FIG. 1. References to vertical direction or height also therefore refer to dimensions or movement along the axis marked Z in FIG. 1. The microplate receiving area 20 is arranged to be height-adjustable, by mounting the microplate receiving member 21 on a track 22. The receiving member 21 is provided with a complementary track engaging member 23, for engagement with the track 22, to allow the receiving member 21 to slide in a vertical direction, that of the Z axis marked in FIG. 1, to adjust the height of the receiving member 21, receiving area 20 and the corresponding microplate 30, with respect to the body 10 of the device 1 and the remaining components attached thereto.

Movement of the receiving member 21 relative to the track 22 can be controlled in a number of ways. A relatively simple way can be through a frictional engagement between track 22 and corresponding track engagement member 23. By providing a frictional resistance which is greater than the weight of the receiving member 21, microplate 30 and its contents, the position of the receiving area 20 relative to the body 10 of the device 1, and thus relative to the agitation members 41 of the agitation member 40, allows height-adjustability, while having minimal cost.

The receiving area 20 can then be moved relative to the body 10 of the device by simply providing an input force which is greater than the frictional force between the track 22 and the track engagement member 23 plus the weight of those components and the microplate to move the platform in an upward direction, and minus the weight of the platform to move the platform in a downward direction. This could be provided by a simple manual input, or in the alternative, by electrical input with the use of linear motors, screws, thread drives combined with a rotational motor, or any other suitable means of linear actuation, such as hydraulic or pneumatic drives, pulley belts for turning rotational input to linear movement, as some examples. Screw thread means such as a ball screw can be beneficial. However, these can result in high forces in the vertical direction which, when combined with fine elongate projections, can cause a safety concern. Means for limiting the vertical forces can be included such as a limited torque clutch or a linear force limiter which allows linear slippage of the moving parts when forces are too great. A belt and pulley arrangement can reduce the vertical forces achieved by the drive and can therefore be preferable. A lead screw can also be beneficial since stiction in such arrangements can be relatively high and so helps to retain the linear drive in a fixed height without input or need for separate locking means.

The agitation member 40 is provided with an array of agitation projections 41. The agitation projections 41 are arranged to enter into the wells 31 of the microplate 30. An array of agitation projections 41 is provided corresponding to the array of wells 31, such that each well 31 is paired with a corresponding agitation projection 41. In this way, when the receiving platform 21 is raised vertically along track 22 towards agitation projections 41, the agitation projections 41 are introduced into wells 31. Relative movement of the agitation projections 41 with respect to the microplate 30 can then act to agitate contents of the wells 31 of the microplate 30.

Figure 2:
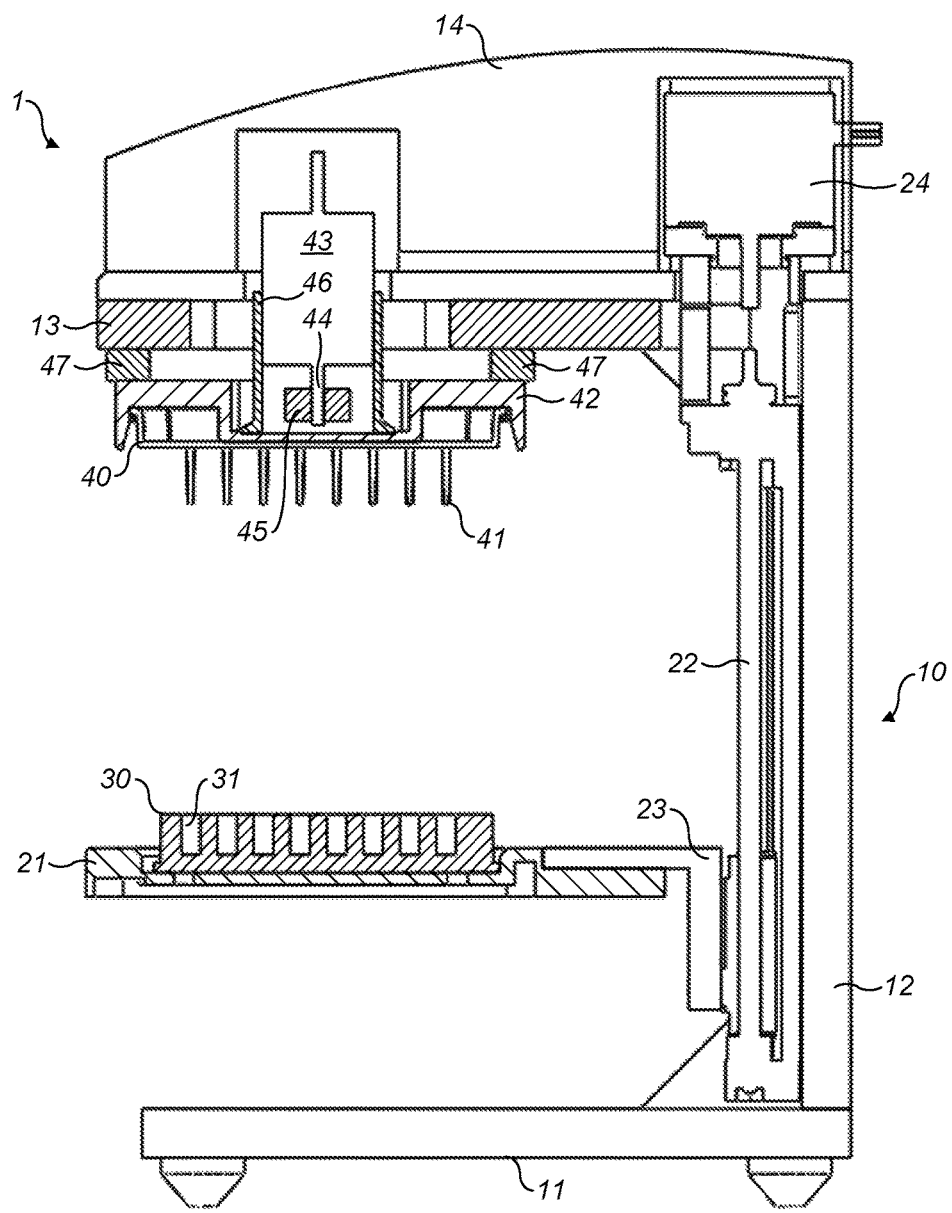
FIG. 2 shows a side view section of the device of FIG. 1.

FIG. 2 illustrates a side-view section through the device 1 of FIG. 1. In FIG. 2, further detail of the adjustment and agitation mechanisms can be seen. In the illustrated example, the linear actuation of track engagement member 23 on linear track 22 is provided by a motor 24. Rotational motion of the motor 24 is translated into linear, vertical, motion. The motor 24 can therefore be electronically controlled to adjust a height of the receiving platform 21 with respect to the main body of the device, and/or with respect to the array of agitation members 41 mounted in the device.

The actuation means for creating agitation input in the illustrated example is provided by a rotary motor 43. Attached to the spindle 44 of the motor is a mass 45. The mass 45 is configured so that its centre of mass is located away from the axis of the spindle 44. It can therefore be termed an eccentric mass, since its centre of mass is located eccentrically with respect to the spindle of the motor 43. Rotation of the eccentric mass relative to the body 43 creates a vibrating motion due to the vibrations induced by rotation of the centre of gravity of the mass 45 around the spindle 44. This vibration is translated to the agitation member receiving member 42 via a motor mount 46. Agitation member receiving member 42 is arranged for receiving the agitation member 40. The vibrations are then transmitted onto the agitation member 40 and the agitation projections 41, provided as pins mounted to the agitation member 40, which in the illustrated example is a plate. This mechanical connection from actuating means to agitation members creates an effective and low cost means for transmitting vibrations or oscillations from the actuating means to the array of agitation members.

It is beneficial to transmit the vibrations of the eccentric mass 45 to the agitation projections 41 via the means described above. However, it is not necessarily beneficial to transmit those vibrations to the body 10 of the device 1. Therefore, vibration dampers 47 are provided between the agitation member receiving member 42 and the upper horizontal member 13. The function of vibration dampers 47 can be two-fold. Firstly, they permit translational movement between the agitation member receiving member 42 and the body 10. They also have a damping or isolating function, to isolate the vibrations induced in the motor 43 from the body 10, so that vibration is not unnecessarily transmitted to the body 10. When vibration is transmitted to the body, this can create noise, energy wastage, potential excessive wear and damage to components of the device which are not intended for vibration. The ideal case is complete elimination of any vibration being transmitted to the body. However, in practice, some degree of transmittal of vibration to the body 10 may be tolerated to allow the cost of dampers 47 to be reduced.

The vibration dampers 47 can be configured in a number of ways to induce different types of movement in the agitation projections 41. Where the dampers 47 create equal damping forces in all lateral directions, the circular motion of the eccentric mass 45 can induce a substantially circular stirring motion in the agitation projections 41. Alternatively, if different resistance to lateral forces is provided in different lateral directions in the dampers 47, then greater movement can be permitted in one lateral direction as opposed to others. For example, a substantially oval stirring motion may be induced by using a substantially rectanguloid or oval cross-section in the damping members, so that greater movement is permitted in one lateral direction as opposed to another. In this manner, non-circular stirring motions can, for example, be used for non-circular wells. Oval wells, for example, my require greater motion along the longer dimension of the oval shaped wells.

The vibration dampers 47 can be manufactured from substantially rectanguloid blocks of rubber or other resilient material, which may be simply bonded to their neighbouring components, namely the upper horizontal member 13 of the body 10 and the agitation member receiving member 42. They could also be attached by attachment means such as a bolt provided through the two members 13 and 42 and also passing through the middle of the vibration damper 47. Other methods of construction can be envisaged, such as separate fixing means at the top and bottom ends of the vibration dampers or suspending the dampers by other fixing means.

The eccentric mass actuator illustrated in the preferred embodiment can be manufactured in a relatively low cost manner and can be used in combination with a relatively low cost construction of vibration damper. The actuator of the invention is arranged to provide a substantially horizontal agitation movement in the agitation projections 41, by orientation of the axis of rotation of the eccentric mass in a vertical direction. However, it is also possible to orient the axis of the motor 43 in a substantially horizontal direction so that the oscillations are in a substantially vertical direction. Vertical orientation of the axis of rotation of motor 43 can help to minimise vibrations being transmitted into the body 10 of the device, which reduces noise. Vibration and noise transmitted to the surrounding environment can also be minimised by use of vibration damping in the feet 15 of the device. Other means can be provided to achieve the oscillatory motion of the agitation projections. For example, an eccentric pin can be provided on the shaft 44 of the motor 43, the eccentric pin can be received in a bearing of the agitation member receiving member 42, so that, when the motor 43 is in a fixed position, the eccentric movement of the pin around the shaft 44 induces movement in the agitation member receiving member 42. However, this direct mechanical connection can transmit additional vibrations to the body 10 of the device and so the eccentric mass solution can be advantageous in terms of reducing vibration transmitted into the body of the device.

As already described, in the illustrated example, the agitation member 40 has a substantially solid planar form for retaining the agitation projections 41, and can be termed a plate. Agitation projections 41 of the illustrated example can be termed pins. The illustrated plate is substantially planar in the region of the array of agitation projections 41, but material could be omitted from the plate in between the agitation projections to economise on materials. The function of the agitation member or plate is to retain the agitation projections at substantially fixed distances from one another. During use of the device, the agitation projections 41 come into contact and parts of the agitation projections are located in close proximity to the products being stirred in the wells 31 of the microplate 30. Therefore, the agitation member and its agitation projections are likely to be replaced on a regular basis to enable cleaning in between agitation operations on same or differing batches of product and different wellplates. To enable this replacement, releasable attachment means, for releasably attaching the agitation member 40 to the agitation member receiving member 42 are provided. These will be described later in greater detail.

FIG. 2 shows a partial section through a side view of the device 1 of FIG. 1. Hatching is included to differentiate between certain adjacent components. As can be seen in FIG. 2, the microplate can be retained in the receiving platform 21 by provision of a recess configured to receive the microplate. The recess can be sized and dimensioned to limit lateral movement of the microplate 30 in the recess, so that the relative positions of the agitation projections 41 and the wells 31 can be controlled. This can help to avoid inadvertent contact of the agitation projections with the walls of a well, which can cause unwanted damage to the wells or agitation projections.

Figure 3:
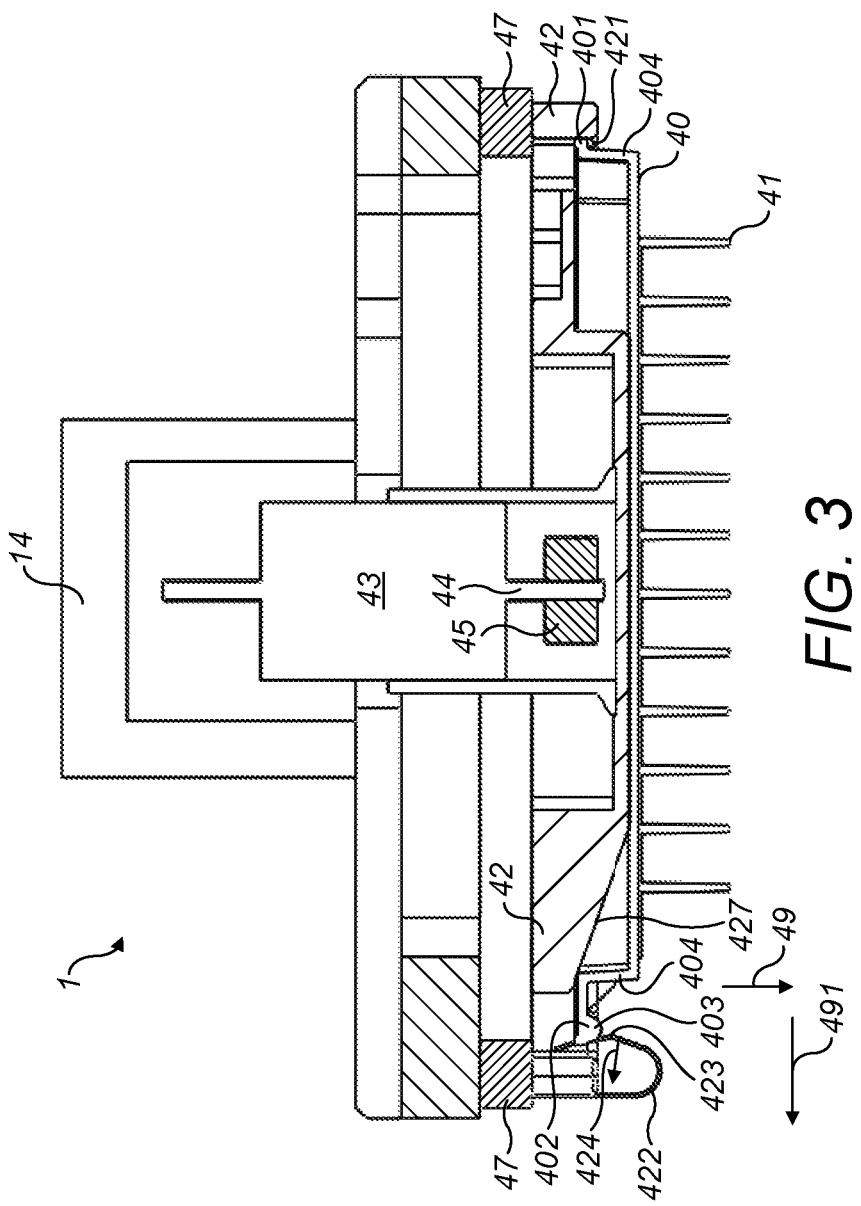
FIG. 3 shows a section illustrating detail of an upper portion of the device of the FIG. 1.
Figure 4:
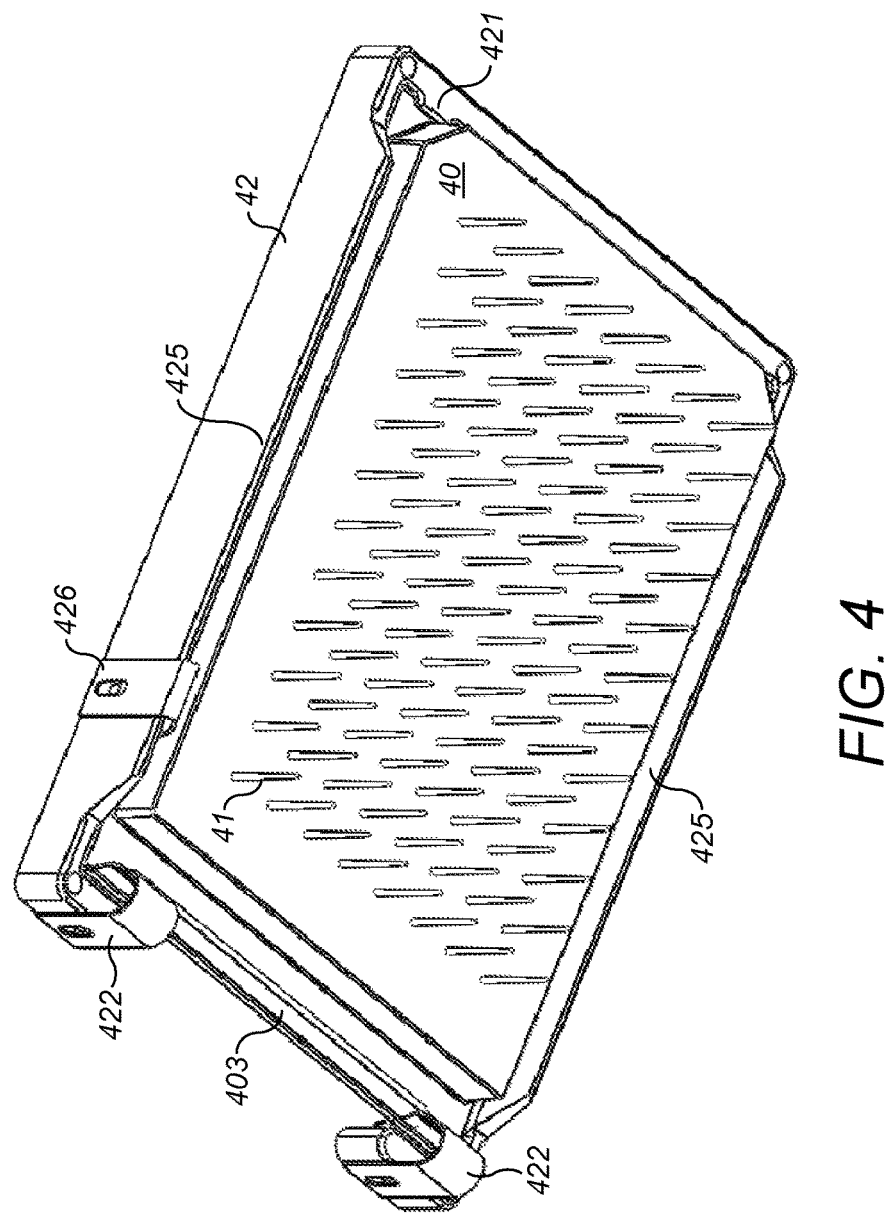
FIG. 4 shows detail of an agitation member and corresponding receiving arrangement of the invention.

FIGS. 3 and 4 illustrate means provided for allowing easy retention and removal of the agitation member 40, and agitation projections 41, from the device 1. The agitation member receiving member 42 is provided with agitation member retaining means. These are provided in the form of a first projection 421 for engaging a corresponding agitation member projection 401 located on one edge of the agitation member. On an opposing edge of the agitation member 40, an opposing agitation member projection 402 engages a resilient biasing member 422. The resilient biasing member 422 acts to retain the agitation member 40 in the agitation member receiving member with a biasing force. The biasing force biases the agitation member 40 towards the first projection 421, so that the first corresponding projection 401 is held in place by the first projection 421. The agitation member biasing member 422 can also be configured, as illustrated, to provide a biasing force in a second direction, upwardly in FIG. 3, to retain the projection 402 within the receiving member 42. The illustrated biasing member 422 is configured so that its biasing force must be overcome in order to extract the agitation member 40 from between the agitation member receiving member 42 and the biasing member 422. To facilitate extraction, the biasing element 422 is configured so that, after initially overcoming the retaining force, by movement of the agitation member through a first amount, the biasing force of the biasing member 422 acts to eject the agitation member 40 from the agitation member receiving member 42. This function is provided by the profile of the biasing member 422 including a curve, ridge or peak 423. When the corresponding projection 402 is above the ridge 423 as shown in the drawing, then the biasing force retains the agitation member in place. During removal, once a user has extracted the agitation member 40 to a degree sufficient that the biasing member has been compressed in a direction of arrow 424, so as to allow the projection 402 to pass over the peak or ridge 423, the biasing force of biasing member 422, in a direction opposite to arrow 424, biases the agitation member out and away from the agitation member receiving member 42 (i.e. downward in FIG. 3). The arrangement can be implemented with one pair of opposing corresponding projections 421 and biasing members 422 provided on the agitation member receiving member 42. However, as illustrated in FIG. 4, the preferred embodiment can include more than one biasing member 422. Each biasing member 422 can be provided with an opposing projection 421, so that the agitation member 40 is more securely retained in the agitation member receiving member 42. The agitation member retaining projections 421 and opposing biasing members 422 can be provided at a first set of opposing locations on substantially opposite sides of the agitation member 40. A second set of agitation member retaining projections 421 and opposing biasing members 422 may be provided. A gap may be provided between first and second biasing members 422, to allow a user to grasp an edge of the agitation member 40 to remove or insert the agitation member in the receiving member 42. The agitation member receiving member 42 can also be provided with guides 425. The guides 425 can be arranged on substantially opposing sides, adjacent to sides on which the projections 421 and biasing means 422. In this way, the guides 425 can assist with guiding the agitation member 40 towards or away from agitation member retaining projections 421. The guides 425 can also assist with guiding the agitation member 40 into place so that its respective projections 401 and 402 align correctly with their corresponding projections 421 and biasing members 422.

A further biasing member 426 can be provided on at least one further side to provide a biasing force on the agitation member 40 in a second direction, different from the direction of the biasing force provided by a first biasing member 422. This may be provided on one of the guides 425. The direction of the biasing force of the further biasing member 426 may be a second direction different to the direction of the biasing force of the first biasing member 422. This can provide more secure retention of the agitation member 40 in the agitation member receiving member 42. In the illustrated example, the direction of the biasing force of the further biasing member 426 is substantially perpendicular to that of the first biasing member 422. This can retain the agitation member 40 against two non-parallel, or perpendicular, sides of the receiving member 42 to more securely hold the agitation member 40 in place. In this way the agitation member can be biased and aligned against sides or a corner of the agitation member receiving member, so that it's alignment with the microplate can be defined and controlled. A similarly arranged biasing arrangement can be used to align the microplate in the microplate receiving area, so that the microplate is biased into a registration corner of the microplate receiving area, or against two sides of the microplate receiving area.

Figure 5:
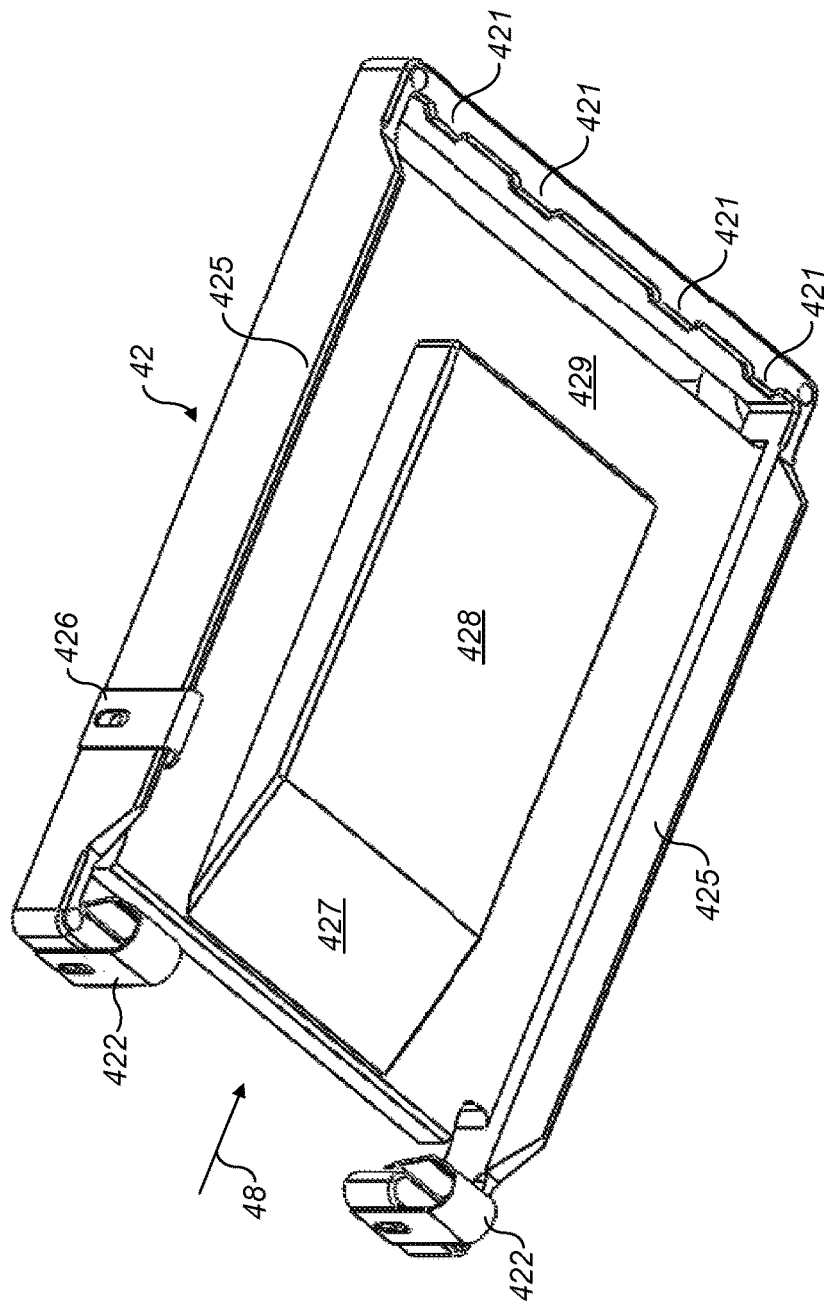
FIG. 5 shows detail of the agitation member receiving arrangement of the device of FIG. 1.
Figure 6:
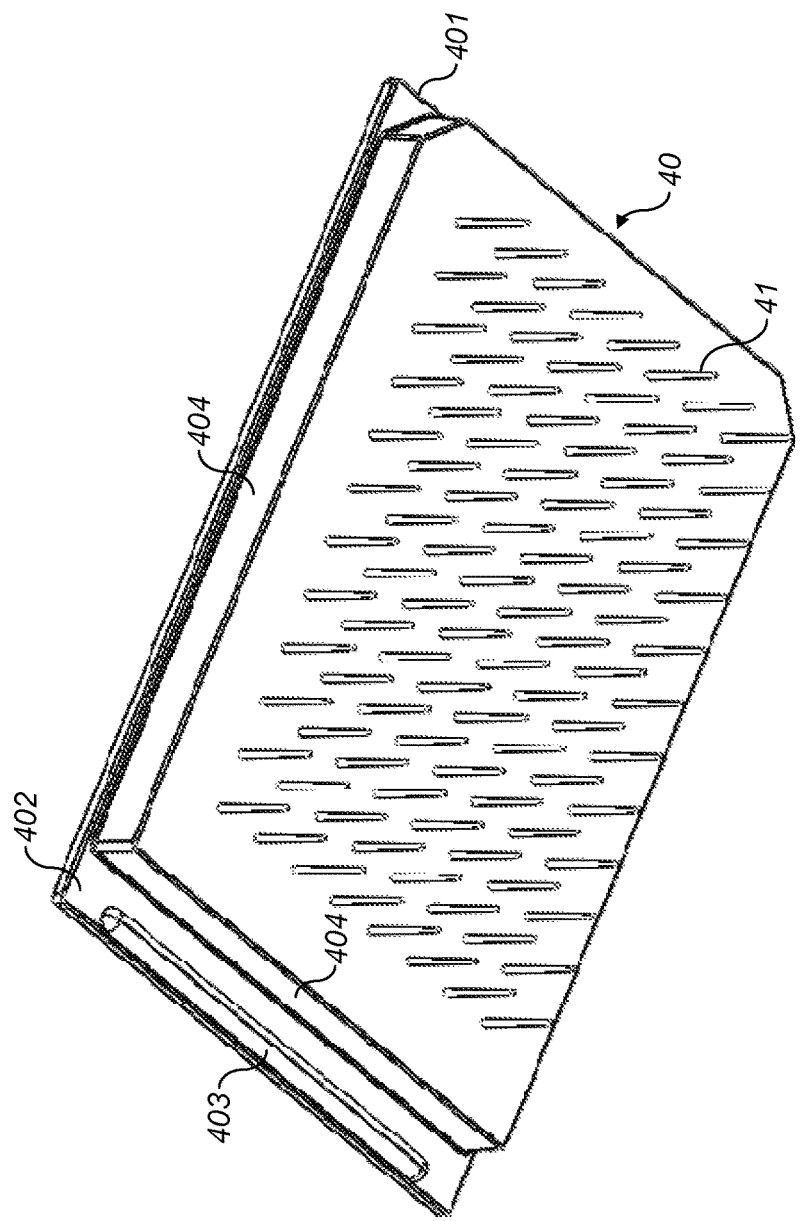
FIG. 6 shows an agitation member and comprising an agitation projection array, for use in the present invention.

As can be seen in FIGS. 3, 4 and 6, the agitation member 40 has grip means, in the form of a lateral ridge 403 provided on an edge of the agitation member, adjacent the projection 402. The ridge at 402 at a first side of the agitation member can act as a grip for a user to extract the agitation member from the receiving member 42. At a second side, distal from the first end, a smaller projection 401 is provided simply for engaging the retaining projection 421 of the receiving member 42. Receiving member 42 is configured so that the agitation member 40 can be slid into the receiving member 42 in a lateral direction, illustrated by arrow 48 in FIG. 5. The agitation member 40 can be extracted by pulling the first end of the agitation member in a downward direction in FIG. 3, away from the receiving member 42, in the direction of arrow 49 and then, once the first end is clear of the biasing member 422, extracting the agitation member laterally, in the direction of arrow 491, to clear the retaining projections 421.

The agitation member has a substantially planar central section on which the agitation members 41 are mounted. An agitation member wall 404 extends from the central section, substantially perpendicularly to a plane of the central section, to retain the agitation member on and within receiving member 42. The receiving member comprises a projecting central portion 428 for engaging the central section of the agitation member 40.

To further enable correct retention and alignment of the agitation member 40 with the agitation member receiving member 42, a sloped portion 427 can be provided on the projecting central portion 428 of the agitation member receiving member, as illustrated in FIGS. 3 and 5. As can be seen in FIG. 3, the sloped portion 427 allows the agitation member 40 to be properly inserted and retained in the agitation member receiving member 42 without undesirably jamming against a vertical side of the central portion 428 upon sideways insertion to the receiving member 42. Optionally, an edge of the agitation member wall 404 can engage the sloping section when biased against it by biasing member 422, although this is not essential and the agitation member may not contact sloped portion 427 at all. The sloped portion 427 can also help to allow for variations in shape and dimensions of the central and wall sections of the agitation member 40 as seen in the side-section profile of the agitation member 40 shown in FIG. 3, due to manufacturing tolerances or inaccuracies.

The sloped portion 427 may allow the biasing member 422 to bias the first end of the agitation member in an upward direction in FIG. 3 and also towards projection 421, whilst providing a secure surface 427 against which the first end can rest. This can allow for some flexibility in the exact dimensions of the agitation member 40, whilst still ensuring that the agitation member 40 is held securely against the receiving member 42 by the biasing member 422. The sloped portion also allows the agitation member 40 to be slid into the receiving member 42 in a lateral direction without the second end of the agitation member and its projection 401 being obstructed by undesirably abutting any vertical side of the projecting portion 428 of the receiving member 42 as the agitation member is introduced onto the receiving member 42.

FIG. 6 shows an agitation member 40 incorporating agitation projections 41 for use in the present invention. The ridge 403 can be seen applied to the projection 402 at a first end of the member 40, while a less pronounced projection 401 is provided at an end distal from the first end of the member, for engaging projections 421 of the agitation member receiving member 42. Wall 404 can also be seen, which extends substantially perpendicularly from the preferably substantially planar, central, portion of the member. Wall 404 may extend fully around a whole perimeter edge of the central portion of the central portion, which may be substantially planar, or wall 404 may extend only from parts of the central portion of the agitation member 40. The wall 404 and planar central section can make up a connecting portion for the agitation member 40.

As can be appreciated from the drawings, the invention provides a novel means for agitating products held in wells 31 of a microplate 30. The array of agitation members 41 can be quickly and easily replaced or removed for cleaning or disposal by means of the releasable retaining features made up of projections 421 and biasing means 422 and the remaining items discussed with regard to FIGS. 3 to 6.

Figure 7C:
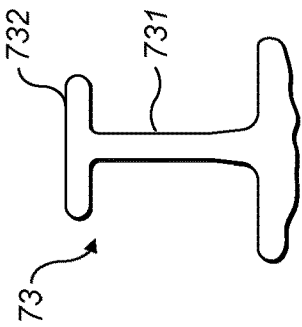
FIGS. 7A to 7C illustrate different forms of agitation member which may be applied to an agitation member of the invention.
Figure 7B:
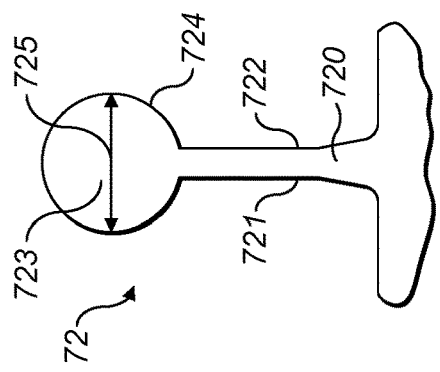
Figure 7A:
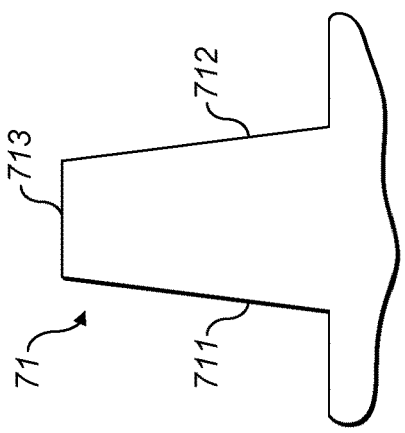

FIG. 7A shows a form of agitation projection 71 which may be used in place of the substantially cylindrical, conical or pin-shaped projections which are shown in the preceding figures. The projection in FIG. 7A has a substantially planar form and has substantially straight sides 711 and 712, which may be substantially parallel or which may converge or diverge toward the distal end 713 of the agitation projection.

FIG. 7B shows an alternative form of projection 72, which can have a support portion 720 having sides 721 and 722, which are substantially parallel, diverging or converging. The projection can have an end portion 724 which is substantially planar, and which may have a greater width 725 in the planar direction which is greater than the width of the support portion. The outer form of the end portion 725 may be curved, circular, oval, rectangular or rectanguloid in form FIG. 7C shows a substantially T-shaped projection 73, which can have a support portion 731 of relatively small width and a further portion 732, oriented in a different direction, preferably substantially perpendicular to the support portion 731.

These various forms of projection can assist with improving the agitation of products contained in the wells of the microplate or in the vessels.

Figure 8:
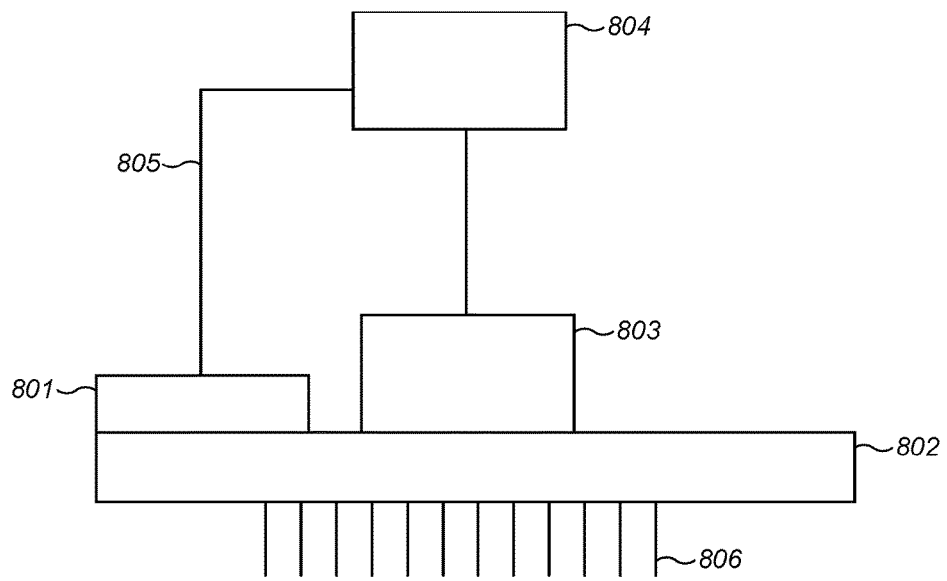
FIG. 8 shows a schematic illustration of a system for controlling a device of the present invention.

FIG. 8 shows a schematic illustration of a control system which can be used to control the actuation of the device of the present invention, particularly to maintain the agitating motion at a resonant frequency of the device. The system includes an accelerometer 801, which is attached to the agitation member receiving member or to the agitation member itself, 802, but generally to any part which is moving with the agitation projections 806 of the device. The actuation means 803 is also connected to the agitation member receiving member 802. The actuation means 803, which may be a motor within an eccentric mass mounted to its shaft, or could alternatively be the direct drive mechanism described herein, is controlled by a processor 804. The processor 804 takes an input from accelerometer 801. The signal 805 from the accelerometer 801 is indicative of a magnitude or amplitude of oscillations in the agitation member, preferably as induced in the agitation member 802 by the input of the actuating means 803. The processor 804 can be configured to drive the actuating means 803 through a sweep of its range of operating speeds or frequencies, from its lower operating speed or frequency, to its upper operating speed or frequency. While controlling the sweep of those frequencies, the processor 804 monitors the signal 805 from the accelerometer 801. Where a peak in amplitude of the oscillations of the agitation member is detected in the signal 805, the corresponding frequency for speed at which the actuating means 803 is being driven can be recorded as a resonant speed or frequency of the system. The processor can therefore be configured to drive the system at the resonant frequency once detected. The system can further be configured to carry out a periodic sweep of the range of operating speeds or frequencies of the actuating means 803 to verify periodically the resonant frequency of the system.

Controlling the system in such a way can improve the effectiveness of the agitating motion for a given drive input. Further, regular scheduled checks of the resonant frequency can ensure that the device is driven at its resonant frequency even if that resonant frequency changes. This change could be due to the use of components of the system having masses which are different from those used when the machine was last calibrated. For example, changing agitation member 40 for one having a different mass would affect the resonant frequency. Further, flexible components of the device changing in stiffness would also affect the resonance. By maintaining the system at its resonant frequency, the amount of agitating power output through the agitating member 802 and its agitation projections 806, can be maximised, and so the agitation of the products in the sample vessels can therefore also be at its most effective and efficient during the operation of the device in different physical conditions or configurations.

Figure 9:
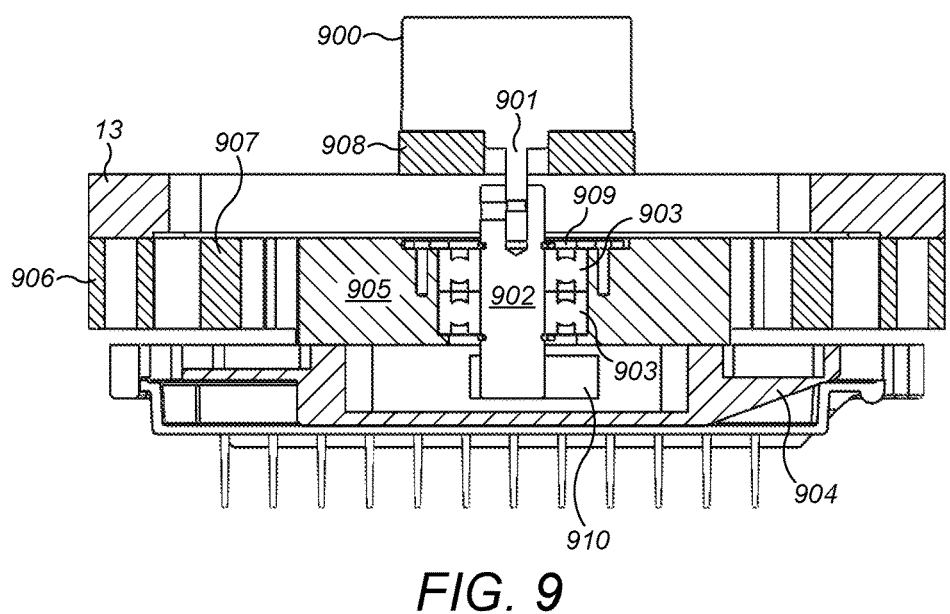
FIG. 9 illustrates an arrangement for providing a direct drive agitating motion in a device of the present invention.

FIG. 9 shows greater detail of an arrangement which can be provided to implement a direct drive agitation input mechanism for the device of the present invention. FIG. 9 shows a front view cross-section through the assembly. The actuating means in this instance is provided in the form of a motor 900. Connected to an output shaft of the motor 901 is an eccentric portion 902. This portion 902 is mounted eccentrically so that rotation of the motor shaft 901 creates a translational movement of the bearing(s) 903, which are mounted to the eccentric shaft 902. The bearings 903 may be roller bearings or friction bearings made from a low frictional material. Rotation of the eccentric shaft 902 in the bearings 902 relative to the bearings 903 provides a translational motion, in a substantially circular path, to the agitating member receiving member 904, to which the bearings 903 are mounted via mounting block 905. The mounting block 905 forms a substantially central portion of a translational coupling of the invention. The translational coupling comprises an outer frame portion 906, which is coupled to the mounting block 905 via leaf spring portions 907, which will be described in greater detail in relation to the following figures. Accordingly, a direct drive connection can be provided between the actuating means 900 and the agitating member receiving member 904 to provide a direct drive input, which can accurately control the motion of the agitating member receiving member 904. The actuating means 900 can be mounted to the upper horizontal member 13 of the device illustrated in FIGS. 1 to 3 in the manner illustrated, via a mounting member 908. A counterbalance 910 can also be mounted eccentrically to the output shaft 901 of the motor 900. This can help to balance the eccentric mass of the eccentric shaft 902, which can help reduce vibrations in the device.

Figure 10:
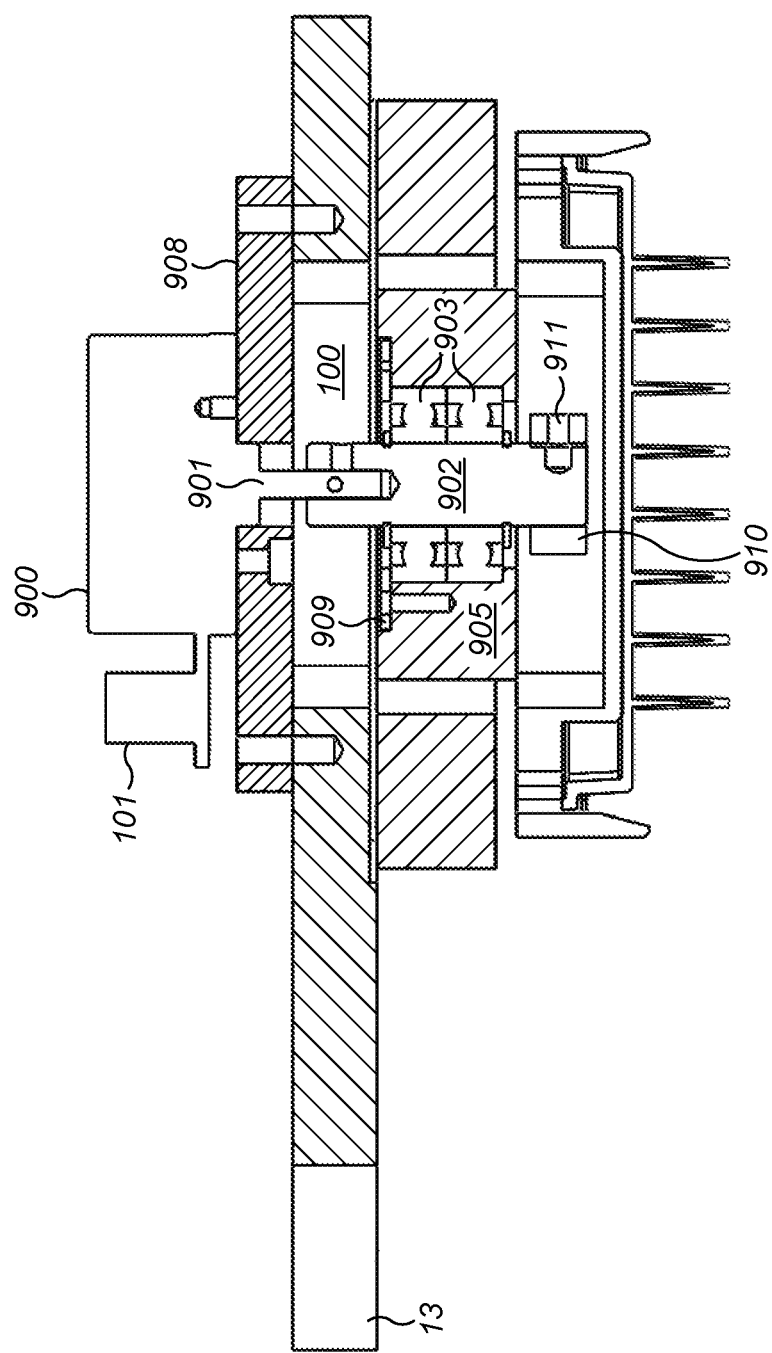
FIG. 10 shows a side view of the device of FIG. 9 in cross-section.

FIG. 10 illustrates a side view of the arrangement of FIG. 9, where it can be seen that the mounting member 908 is mounted over an opening 100 in the upper horizontal member 13, so that the shaft 902 can rotate freely in the opening 100 to translate its eccentric rotational motion through to bearings 903 and the moveable part of the translational coupling 905. A connector 101 may be provided on the actuating means 900 to connect this to a control circuit and power source. As shown in the figure, the eccentric counterbalance 910 can be held to the eccentric shaft 902 by a grub screw 911 disposed in a threaded hole in the counterbalance.

Figure 11:
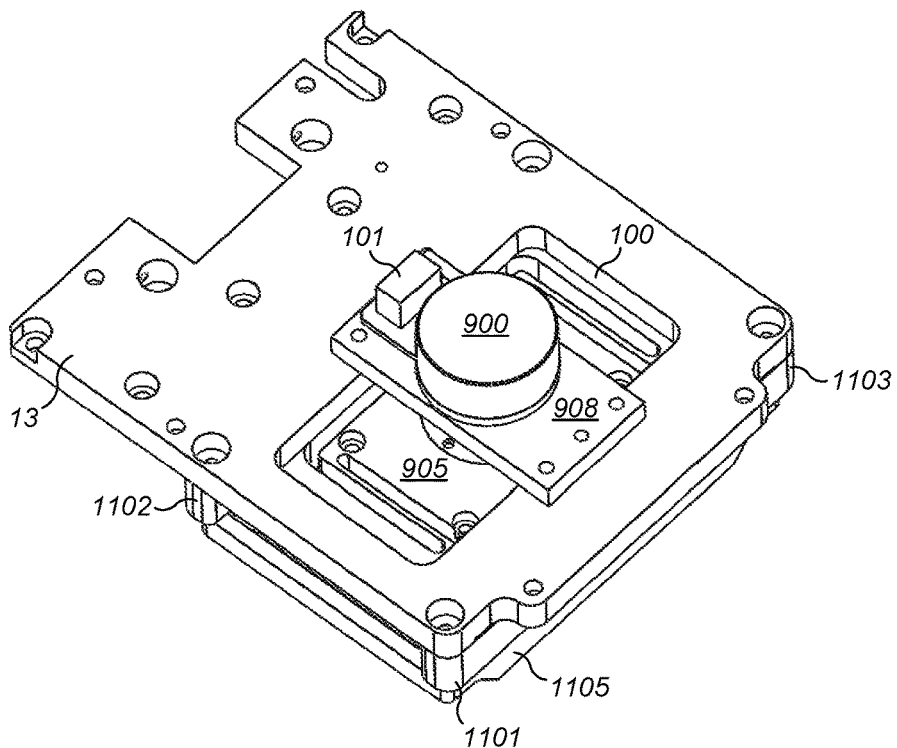
FIG. 11 shows a perspective view of the arrangement of FIGS. 9 and 10.

FIG. 11 shows a perspective view of the arrangement of FIGS. 9 and 10. Here it can be more clearly seen how the motor 900 is mounted over an opening 100 in the upper horizontal member 13 of the device. The output shaft of the motor 900 connects into the central portion 905 of the translational coupling as described above. The translational coupling will be described in greater detail in the following figures. The outer frame comprises connecting points at each corner 1101, 1102 and 1103 (and at a fourth corner not visible in this figure) of the translational coupling, to connect it to the upper horizontal member 13 of the device. The agitation member receiving member 904 and the agitation member 1105 are retained in place by the translational coupling.

Figure 12:
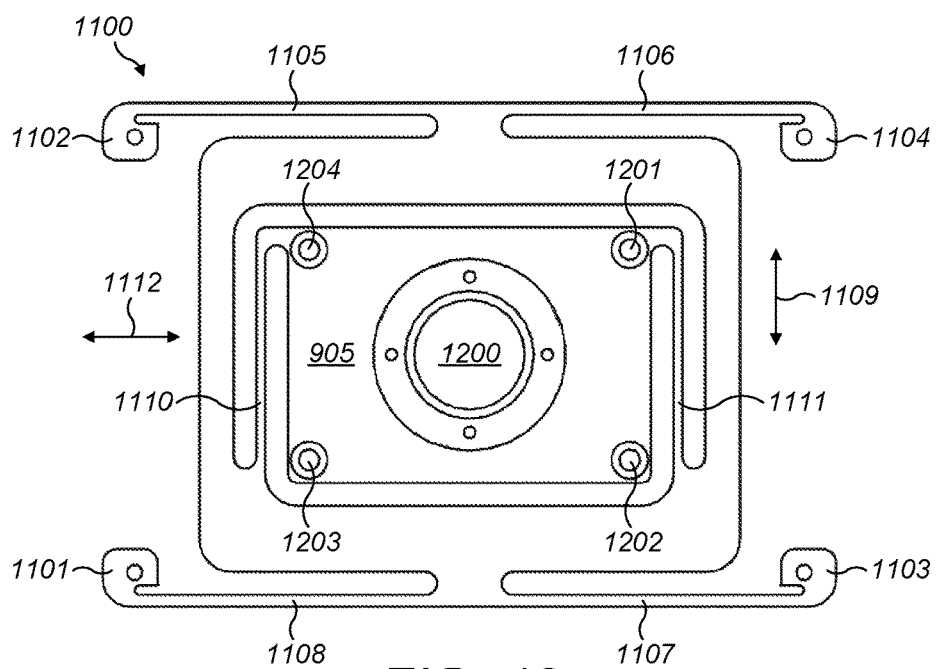
FIG. 12 shows a translational coupling for the arrangement of FIGS. 9 to 11.

FIG. 12 shows a first example of a translational coupling for use in the assembly shown in FIGS. 9 to 11.

The translational coupling 1100 comprises connecting points 1101, 1102, 1103 and 1104, which are arranged to be connected to the upper horizontal member 13 of the device. Those mounting points are connected to a central mounting block 905 of the coupling via leaf springs. In this example, a first set of leaf springs 1105, 1106, 1107 and 1108 allow movement of the central block 905 in a first translational direction in the direction of arrows 1109. A further set of leaf springs 1110 and 1111 is arranged to permit translational movement of the mounting portion 905, which forms a central portion of the translation coupling in a second direction, different to a first direction, and in this particular case perpendicular to the first direction, as illustrated by arrows 1112. The second set of leaf springs permits movement of the mounting portion 905 relative to the first set of leaf springs 1101, 1102, 1103 and 1104. The central mounting block 905 comprises an opening 1200 for receiving the output shaft 902 and the bearings 903 illustrated in FIGS. 9 to 11. These can all be held in place by a retaining plate 909 as illustrated in FIG. 10.

A plurality of moveable connection points 1201, 1202, 1203 and 1204 is also provided for connecting the agitation member receiving member 904 to the mounting portion 905.

Figure 13:
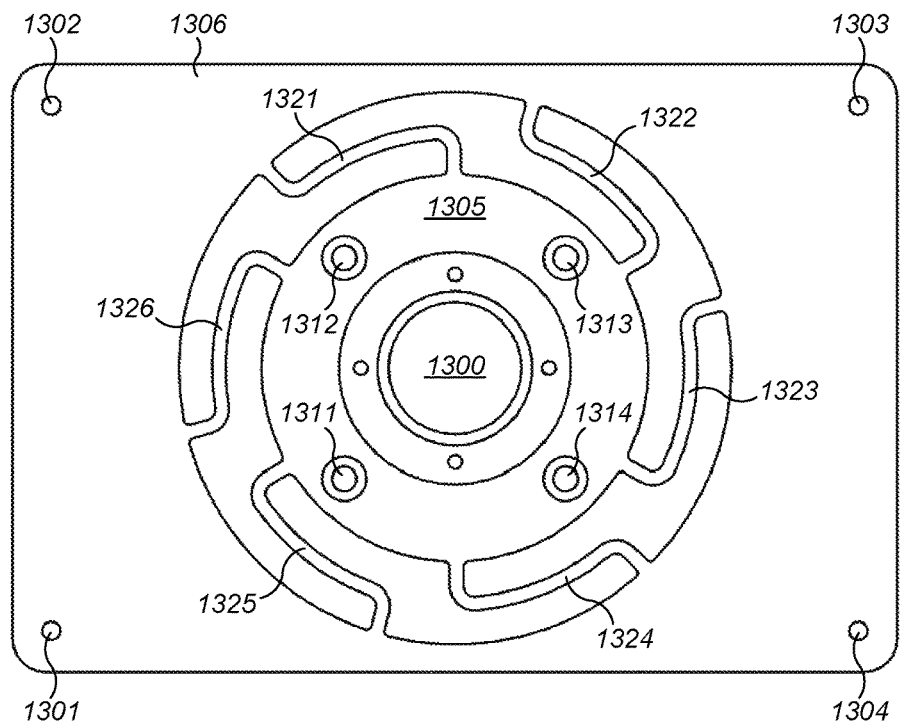
FIG. 13 shows an alternative translational coupling for the arrangement of FIGS. 9 to 11.

FIG. 13 shows an alternative configuration for a translational coupling for use in the arrangement of FIGS. 9 to 11. Outer, fixed, connection points 1301, 1302, 1303 and 1304 are provided in a relatively fixed portion of the coupling. A central mounting block 1305 is provided and comprises an opening 1300 for receiving the bearings 903 and the eccentric shaft 902 as illustrated in FIG. 9. These can be retained in place by the covering plate 909 as illustrated in FIGS. 9 and 10. A set of central, moveable, fixing points 1311, 1312, 1313 and 1314 are provided for connection to the agitation member receiving member 904. The central portion 905 is connected to the outer, fixed portion 1306 by a plurality of substantially circumferential leaf springs 1321, 1322, 1323, 1324, 1325 and 1326. Six substantially circumferential leaf springs are shown in the illustrated example, but any number from two upwards may be beneficial. The leaf springs comprise both circumferential portions, which allow for radial movement of the central portion 1305 relative to the outer portion 1306, as well as radially projecting portions, which allow for a degree of translational movement of the central portion 1305 in a non-radial direction, while still substantially preventing rotation of the central portion 1305 relative to the fixed outer portion 1306.

Figure 14A:
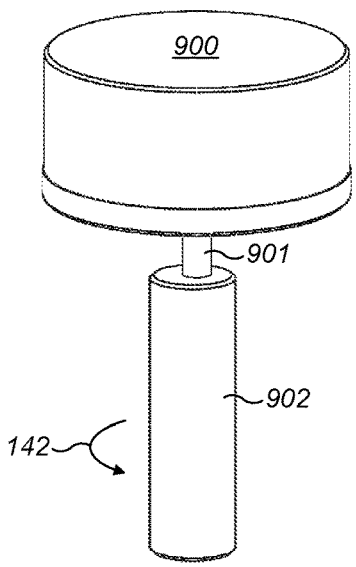
FIGS. 14a and 14b show an actuation means for the drive arrangement of FIGS. 9 to 11.
Figure 14B:
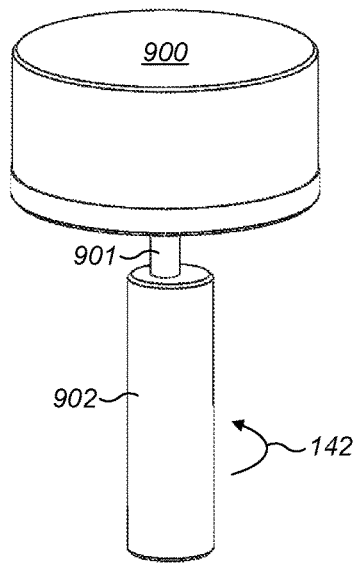

FIGS. 14a and 14b show the rotational motion of the output shaft 901 and the eccentric shaft 902. In FIG. 14a, as the shaft rotates in the direction illustrated by the arrow 141, the output shaft will drive the agitation member receiving member to which it is connected by bearings 903 in a corresponding direction of arrow 141 to draw a circular path. Similarly, in FIG. 14b, the rotation in the direction of arrow 142 will create a motion of the agitation member receiving member in a corresponding direction to arrow 142 to continue the circular path. Such an eccentric shaft can be used to create motions other than simple circular motion. For example, if the shaft is received in an elongate slot rather than in the circular bearings illustrated in FIGS. 9 to 11, then it can be used to create a substantially linear cyclical motion rather than a substantially circular stirring motion.

The device facilitates a method of agitating products in a microplate as described in the following. Products to be agitated can be placed in wells 31 of microplate 30. Microplate 30 can then be placed in receiving area 20 of the device 1. The receiving area 20 can be advanced towards the array of agitation projections 41 to locate the array of agitation members 41 on the array of wells 31 of the microplate 30. Activation of the actuating means 43 induces an agitating motion in agitation projections 41. This is done while the microplate 30 is held substantially still by the receiving member 21. This mode of operation is advantageous compared to other known methods in which the well plate is agitated, which can result in spillage of the products from the wells 31 if a high level of agitation is applied. This is because the whole mass of the products to be agitated in the wells 31 is moved and so there is a greater likelihood of the products being ejected from the wells 31. Greater agitations can be applied by agitation of the agitating projections 41, while retaining the microplate 30 substantially still, while reducing the risk of products being inadvertently ejected from the wells 31. The actuating means 43 can be activated at varying speeds to induce varying rates of agitation. The degree of eccentricity of the eccentric mass 45 can also be varied to create a varying amplitude of vibration at any given rate of rotation. In this way, the device can be adapted to agitate differing liquids, fluids, emulsions, etc. The apparatus may also be useful for cell lysis, cell resuspension, compound resuspension and for re-rendering compounds to a soluble state.

Figure 15A:
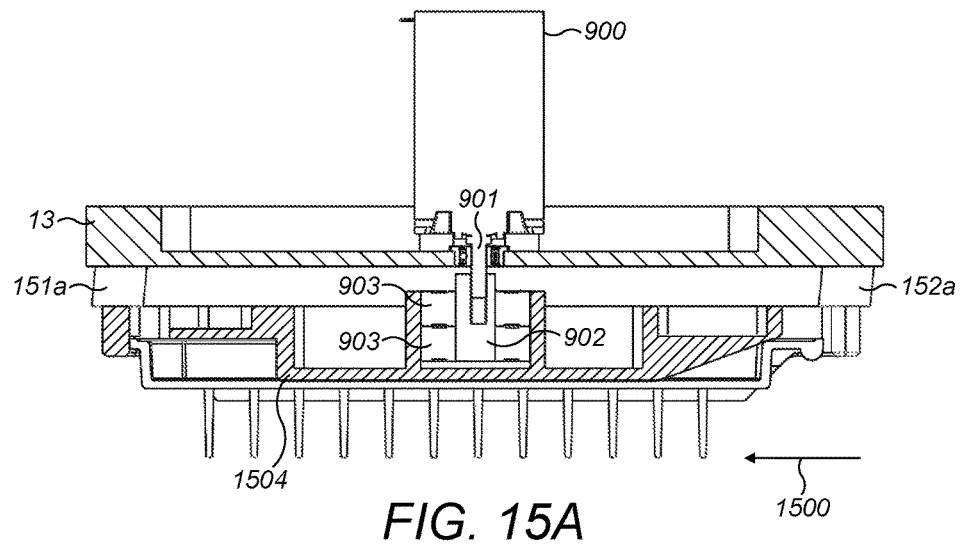
FIGS. 15A to 16B show alternative translational coupling means for the device of the invention.

FIG. 15A shows an alternative arrangement of a translational coupling which can be used in the assembly shown in any of FIGS. 9 to 11. The translational coupling connects the upper horizontal member 13 to the agitation member receiving member 1504 via flexible couplings 151a and 152a as shown in the drawing. In practice, a number of flexible couplings 151a and 152a may be provided at an array of locations between the body of the device and the agitation member receiving member 1504. The flexible couplings may be resilient couplings made from a resilient material. As with the arrangement shown in FIGS. 9 to 11, the direct drive connection is provided from a motor 900, via its output shaft 901, and an eccentric shaft 902, which is received in rotational bearings 903. As can be seen in FIG. 15A, rotation of the eccentric shaft 902 has driven the agitation member receiving member 1504 left in the Figure in a direction of arrow 1500. The related deformation of the flexible couplings, to allow the relative movement between the upper horizontal member of the body and the agitation member receiving member can be seen in the figure.

Figure 15B:
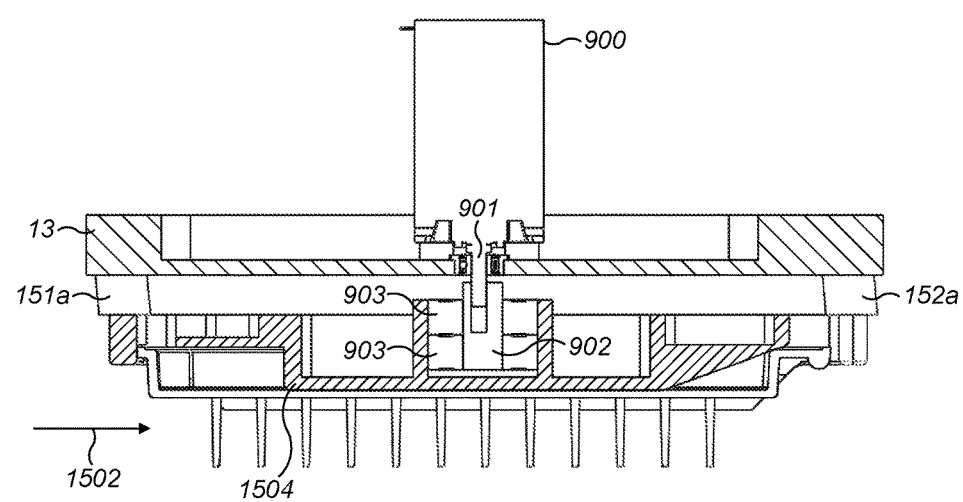

FIG. 15B illustrates the arrangement of FIG. 15A, wherein the output shaft 901 and the eccentric shaft 902 have rotated through substantially 180° about the axis of rotation of the output shaft 901, to drive the agitation member receiving member 1504 to the right in the Figure, in the direction of arrow 1502. The flexible connection members 151a and 152a therefore act as a translational coupling, which allows translational movement of the agitation member receiving member 1504 relative to the body, more particularly the upper horizontal member 13, while substantially preventing relative rotation of the agitation member receiving member 1504 relative to the body of the device. The assembly therefore creates a greater lateral or translational movement and a lesser or zero rotational motion of the agitation member receiving member relative to the upper horizontal member of the body. This is assisted by the provision of a drive mechanism which does not transmit any rotational drive between the actuating means and the agitation member receiving member. This can be achieved by providing means, such as bearings, which permit free rotation of the actuating means relative to the actuating member receiving member, or relative to the upper horizontal member 13 of the body, while still permitting the transmission of a lateral or translational driving force.

Figure 16A:
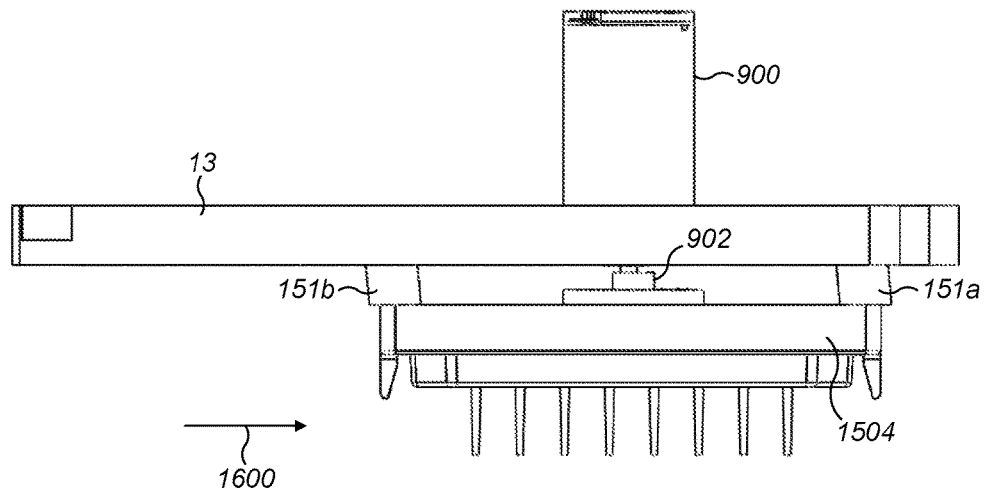
Figure 16B:
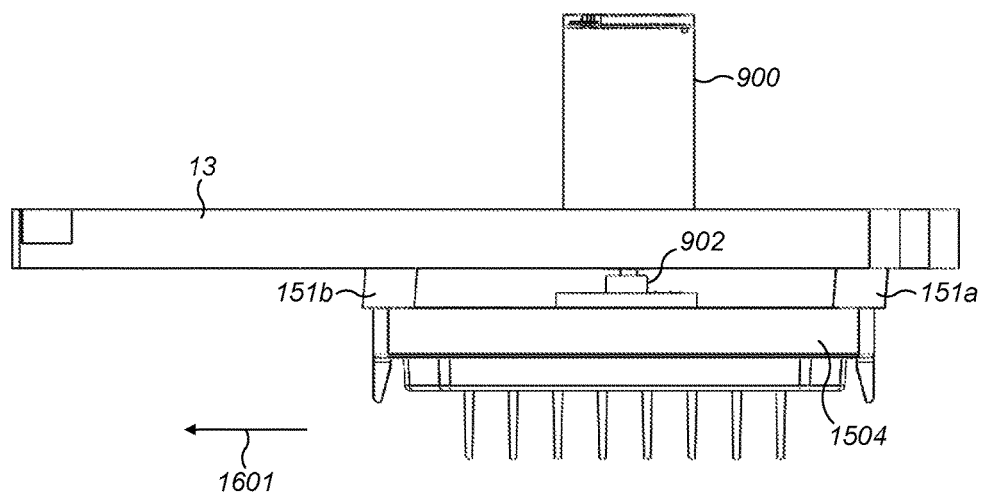

FIGS. 16A and 16B complete the illustration of the degrees of freedom of movement of the agitation member receiving member relative to the upper horizontal member 13 by virtue of resilient members 151a and 151b providing a flexible, preferably resilient, connection between the two. This allows the desired translational relative movement between the components, but restricts rotational relative movement between the two components. In FIG. 16A, the rotation of the output shaft, and its eccentric shaft 902 attached the motor 900, has driven the agitation member receiving member to the right in the Figure as indicated by arrow 1600. As can be seen in FIG. 16B, the agitation member receiving member 1504 has been driven to the left in the Figure in a direction of arrow 1601, by the continued rotation of the eccentric shaft 902. Thus rotation of the eccentric shaft 902 transmits translational, but not rotational movement between the upper horizontal member of the body and the agitation member receiving member.

Although the invention has been described above with reference to one or more preferred embodiments, it will be appreciated that various changes or modifications may be made without departing from the scope of the invention as defined in the appended claims.

The invention claimed is:

1. An agitation device, for agitating products held in an array of sample vessels, comprising:
    a body, comprising a vessel receiving area, adapted to receive an array of sample vessels for holding the products to be agitated;
    actuating means, for creating an agitating motion; and
    an agitation member receiving member, connected to the actuating means, and arranged to receive an agitation member comprising an array of agitation projections, so that when placed on the receiving member, the projections are arranged to enter the sample vessels;
    wherein the device is arranged to hold the sample vessels substantially still relative to the body and to induce an agitating motion in the array of agitation projections via the agitation member receiving member, to agitate products in the sample vessels,
    wherein the actuating means comprises an actuator arranged to directly drive a relative motion between the body and the agitation member receiving member, and wherein the agitation member receiving member is mounted to the body via a translational coupling arranged to permit translational motion of the agitation member receiving member relative to the body, but to substantially inhibit rotational motion of the agitation member receiving member relative to the body.

2. An agitation device according to claim 1, wherein the actuator is fixedly connected to either of the body or the agitation member receiving member and drives the other of the body or the agitation member receiving member, to create a directly driven agitating motion in the agitation member receiving member, relative to the body.

3. An agitation device according to claim 1, wherein the translational coupling comprises a plurality of flexible connections between a movable portion of the device and a fixed portion of the device.

4. An agitation device according to claim 3, wherein the translational coupling comprises a plurality of flexible members connecting the body to the agitating member receiving member.

5. An agitation device according to claim 3, wherein the translational coupling comprises a plurality of leaf springs arranged between a movable portion of the translational coupling and a fixed part of the translational coupling.

6. An agitation device according to claim 5, wherein the leaf springs are arranged to be relatively flexible in a plane of the agitating motion of the device and to be substantially stiff in a direction perpendicular to the plane of the agitating motion of the device to support the agitation member at a fixed distance from the plane of the array of vessels.

7. An agitation device according to claim 5, wherein the plurality of leaf springs comprises a first set of leaf springs configured to permit translational movement of the agitation member receiving member in a first translational direction in a plane of the agitating motion of the device, and a second set of leaf springs configured to permit translational movement of the agitation member receiving member in a second translational direction in the plane of the agitating motion of the device.

8. An agitation device according to claim 7, wherein the second translational direction is perpendicular to the first translational direction.

9. An agitation device according to claim 3, wherein the plurality of flexible connections are configured to permit translational motion of the moveable portion relative to the fixed portion, and to substantially prevent rotational motion of the moveable portion relative to the fixed portion.

10. An agitation device according to claim 3, wherein the fixed portion and the moveable portion form part of the translational coupling by which the agitation member receiving member is mounted to the body.

11. An agitation device according to claim 1, wherein the actuating means is fixedly mounted to the body and is arranged to drive the agitation member receiving member to transmit translational movement, but not rotational movement, thereto.

12. An agitation device according to claim 1, wherein the actuating means comprises a rotary oscillator for creating a rotary stirring motion in the agitation member.

13. An agitation device according to claim 1, further comprising a sensor for detecting a resonant frequency in the agitation device and a controller arranged to control actuating means of the agitation device to maintain the agitating motion at the resonant frequency, in response to input from the sensor.

14. An agitation device according to claim 1, wherein the agitating motion is induced in a substantially horizontal plane of the device.

15. An agitation device according to claim 1, having first and second configurations;

the first configuration permitting the sample vessels and/or the array of agitation members to be removed from the body;

the second configuration maintaining the agitation members in the sample vessels to stir the products in the vessels.

16. An agitation device according to claim 15, wherein the device is arranged to change between the first a second configurations by relative movement of the vessel receiving area and an agitation member receiving member, toward and away from one another.

17. An agitation device according to claim 1, wherein the actuator is connected to the agitation member receiving member by a direct drive connection.

18. An agitation device according to claim 17, wherein the direct drive connection comprises an eccentric portion configured for rotation by the actuator, and one or more bearings by which the eccentric portion is connected to the agitation member receiving member to permit rotation of the eccentric portion relative to the agitation member receiving member.

19. An agitation device according to claim 18, wherein the one or more bearings are mounted on the eccentric portion and on the agitation member receiving member.

20. An agitation device according to claim 19, wherein the one or more bearings are mounted on the agitation member receiving member via a mounting block, the mounting block forming a substantially central portion of the translational coupling.

* * * * *